United States Patent [19]

Morimoto et al.

[11] Patent Number: 4,670,549

[45] Date of Patent: Jun. 2, 1987

[54] METHOD FOR SELECTIVE METHYLATION OF ERYTHROMYCIN A DERIVATIVES

[75] Inventors: Shigeo Morimoto; Takashi Adachi, both of Saitama; Toshifumi Asaka; Masato Kashimura, both of Ageo; Yoshiaki Watanabe, Kodaira; Kaoru Sota, Tokorozawa, all of Japan

[73] Assignee: Taisho Pharmaceutical Co., Ltd., Japan

[21] Appl. No.: 832,322

[22] Filed: Feb. 24, 1986

[30] Foreign Application Priority Data

Mar. 18, 1985 [JP] Japan .................................. 60-53618
Sep. 21, 1985 [JP] Japan ................................ 60-269357

[51] Int. Cl.$^4$ ........................................... C07H 17/08
[52] U.S. Cl. ...................................... 536/7.4; 536/7.2
[58] Field of Search .................................. 536/7.2, 7.4

[56] References Cited

U.S. PATENT DOCUMENTS

| 3,923,784 | 12/1975 | Kierstead et al. | 536/7.4 |
| 4,264,765 | 4/1981 | Bodor et al. | 536/7.2 |
| 4,331,803 | 5/1982 | Watanabe et al. | 536/7.2 |

FOREIGN PATENT DOCUMENTS

| 041355 | 12/1981 | European Pat. Off. | 536/7.2 |
| 147062 | 7/1985 | European Pat. Off. | 536/7.2 |
| 158467 | 10/1985 | European Pat. Off. | 536/7.2 |

Primary Examiner—Johnnie R. Brown
Attorney, Agent, or Firm—Pahl, Lorusso & Loud

[57] ABSTRACT

A method for the selective methylation of the hydroxy group at the 6-position of erythromycin A derivatives which comprises reacting a compound represented by the formula R-X (wherein R is a 2-alkenyl group, a benzyl group or a substituted benzyl group, and X is a halogen atom), reacting the resulting quaternary salt compound with a methylating agent, and then eliminating R groups of the resulting compound to give 6-O-methylerythromycin A 9-oxime, is disclosed.

3 Claims, No Drawings

METHOD FOR SELECTIVE METHYLATION OF ERYTHROMYCIN A DERIVATIVES

BACKGROUND OF THE INVENTION

1. THE FIELD OF THE INVENTION

The present invention relates to a method for the selective methylation of the hydroxy group at the 6-position of erythromycin A derivatives.

2. DESCRIPTION OF THE PRIOR ART 6-0-Methylerythromycins are useful as anti-bacterial agents or intermediates for synthesis of the anti-bacterial agents. For example, 6-0-methylerythromycin A is not only stable in the acidic conditions but also has a strong anti-bacterial activity when compared with erythromycin A. Especially, this compound shows an excellent effect for treatment of infections by oral administration, and therefore it is a useful anti-bacterial agent.

There is known in the past a method for methylating the hydroxy group at the 6-position of the erythromycin A derivative which comprises substituting the hydrogen atom of the hydroxy group at the 2'-position and the methyl group of the dimethylamino group at the 3'-position of erythromycin A derivative by benzyloxycarbonyl groups, and reacting the resulting compound with a methylating agent (U.S. Pat. No. 4,331,803). However, since erythromycin A has many hydroxy groups, there are obtained various kinds of erythromycin A derivatives which are methylated at hydroxy groups at any other than the 6-position as the by-products besides the desired 6-0-methylerythromycin A derivative by the above-mentioned known method. Accordingly, this method requires the complicated procedure for purification of the 6-0-methylerythromycin A derivative, and the yield of said derivative is low.

SUMMARY OF THE INVENTION

An object of the present invention is to provide a novel method for the selective methylation of the hydroxy group at the 6-position of erythromycin A derivatives.

Other objects and advantages of the present invention will be apparent from the following descriptions.

DETAILED DESCRIPTION OF THE INVENTION

The present invention relates to a method for the selective methylation of the hydroxy group at the 6-position of erythromycin A derivatives which comprises reacting erythromycin A 9-oxime with a compound represented by the formula R-X (wherein R is a 2-alkenyl group, a benzyl group or a substituted benzyl group, and X is a halogen atom) to give a quaternary salt compound represented by the formula

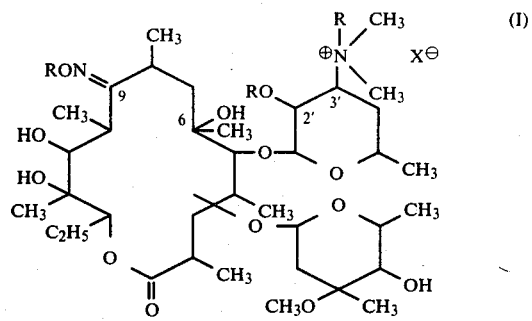

(wherein R and X are as defined above), reacting the resulting compound with a methylating agent to give a 6-0-methylerythromycin A derivative, and eliminating R groups of the resulting compound by hydrogenolysis to give 6-0-methylerythromycin A 9-oxime represented by the formula

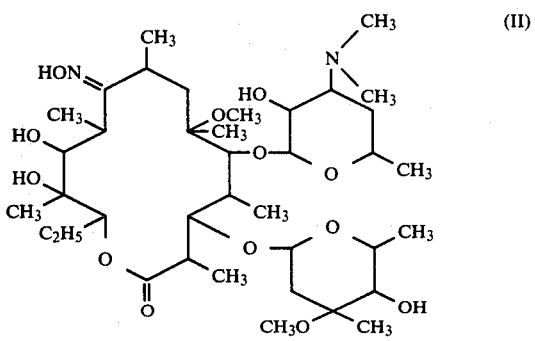

In the specification, the term "2-alkenyl group" includes an allyl, a methallyl, a crotyl, a prenyl, a 2-pentenyl, a 2-ethylbutenyl, a geranyl and a neryl group, the term "substituted benzyl group" includes the benzyl group substituted by one to three of halogen atoms, methyl groups, methoxy groups and/or nitro groups in the benzene ring, and the term "halogen atom" includes a chlorine, a bromine and an iodine atom.

The present invention is illustrated in more detail as follows: erythromycin A 9-oxime in a solvent, together with a compound of R-X, is stirred at from 0° C. to the refluxing temperature of the solvent, a base is added, and the mixture is stirred at from 0° C. to room temperature to give a compound of formula I. The amount of the compound of R-X used is 3–5 molar equivalents, preferably 4 molar equivalents relative to erythromycin A 9-oxime. As the solvents, there can be used acetone, tetrahydrofuran, N,N-dimethylformamide, dimethyl sulfoxide, dioxane, 1,2-dimethoxyethane, dichloromethane, chloroform and a mixture thereof. Examples of the base used are sodium hydroxide, potassium hydroxide, sodium hydride, potassium hydride, potassium t-butoxide and the like. It is sufficient to use 2–3 molar equivalents of the base relative to erythromycin A 9-oxime.

The reaction of the compound of formula I and the methylating agent may be carried out in a solvent in the presence of a base with stirring at from −15° C. to room temperature, preferably from 0° C. to room temperature. As the methylating agent, there can be used methyl bromide, methyl iodide, dimethyl sulfate, methyl p-toluenesulfonate, methyl methanesulfonate and the like. It is sufficient to use 1–3 molar equivalents of the methylating agent relative to the compound of formula I. The bases used are the same as those described above. Although 1-2 molar equivalents of the base are normally used relative to the compound of formula I, but it is preferable to use about 1.3 molar equivalents of the base for the prevention of the formation of the by-products. Examples of the solvent used are polar aprotic solvents such as N,N-dimethylformamide, dimethyl sulfoxide, N-methyl-2-pyrrolidone, hexamethylphosphoric triamide, a mixture thereof or a mixture of one of these solvents and a solvent such as tetrahydrofuran, 1,2-dimethoxyethane, acetonitrile, ethyl acetate and the like.

The elimination of R groups of the resulting 6-0-methylerythromycin A derivative can be carried out by homogeneous or heterogeneous hydrogenolysis known per se. For example, this reaction may be carried out in an alcoholic solvent (e.g., methanol, ethanol and the like) in the presence of a catalyst such as palladium black and palladium carbon under a hydrogen atmosphere with stirring. The addition of formic acid, acetic acid or the like is convenient for the progression of the reaction.

This reaction can also be carried out easily in the presence of a suitable hydrogen source (e.g., ammonium formate, sodium formate, and a mixture of these formates and formic acid) and a catalyst (e.g., palladium carbon, palladium black and the like) in an organic solvent (e.g., methanol, ethanol, N,N-dimethylformamide and the like) with stirring at from room temperature to 70° C.

Furthermore, this reaction may be carried out by using a platinum group compound and a ligand as a catalyst. Examples of the platinum group compound are the salts or complexes of ruthenium, rhodium, palladium and platinum, and examples of the ligand are phosphor compounds such as triphenylphosphine, tri-n-butylphosphine, triethylphosphite, 1,2-ethylene(diphenyl)phosphine and the like. However, a mixture of palladium acetate and triphenylphosphine may usually be used. This reaction can be carried out in the presence of formic acid or a salt thereof. Examples of the salt of formic acid are ammonium salts thereof such as ammonium formate, trimethylammonium formate, triethylammonium formate and the like, and alkali metal salts thereof such as sodium formate, potassium formate and the like.

The 9-oxime derivatives in the present invention are compounds in the syn-form, anti-form or a mixture thereof.

The compounds of formula II are novel compounds which have anti-bacterial activity and can be easily converted into 6-0-methylerythromycin A by deoximation using sodium hydrogen sulfite, titanium trichloride-ammonium ammonium acetate, sodium nitrite-hydrochloric acid, sodium hydrosulfite ($Na_2S_2O_4$) or the like.

The method for methylating a hydroxy group at the 6-positon of erythromycin A derivative of the present invention has very high selectivity when compared with the known method, therefore this method makes it possible to reduce the formation of the by-products and to simplify the purification procedure of the desired 6-0-methyl derivative. Furthermore, although it is necessary to methylate the 3'-methylamino group after elimination of the protective groups of the hydroxyl group at the 2'-position and the amino group at the 3'-position of the intermediate in the known method, since the 3'-dimethylamino group is protected in the form of a quaternary salt in the method of the present invention, it is not necessary to methylate an amino group at the 3'-position after elimination of the protective groups.

Subsequently, the present invention will be more concretely illustrated by the following Examples and a Referential Example.

EXAMPLE 1

(1) To a solution of 10 g of erythromycin A 9-oxime in 100 ml of a mixture of dimethyl sulfoxide/tetrahydrofuran (1/1:V/V) was added 4.6 ml of allyl bromide, and then the mixture was stirred at room temperature for 2 hours. After ice-cooling the reaction solution, 1.41 g of 50% sodium hydride was added, and the mixture was stirred at room temperature for 2.5 hours. The reaction solution, after addition of 150 ml of water, was extracted twice with 150 ml of ethyl acetate. The solvent was evaporated, and there was obtained the crude product, which was then crystallized from chloroform-hexane to give 10.79 g of 2'-0,3'-N-diallylerythromycin A 9-(0-allyl)oxime bromide.

(2) In 42 ml of a mixture of dimethyl sulfoxide/tetrahydrofuran (1/1:V/V) was dissolved 10.5 g of the compound obtained in the above item (1), and then 2.06 ml of methyl iodide and 948 mg of 85% potassium hydroxide powder were added, respectively, under ice-cooling. After stirring for 2 hours, the reaction solution was poured into 150 ml of water and extracted twice with 150 ml of ethyl acetate. The ethyl acetate layer was washed once with 150 ml of a saturated aqueous sodium chloride solution, and the solvent was evaporated under reduced pressure. The resulting crude product was mixed with 40 ml of chloroform and filtered, and the filtrate was concentrated to give 12.72 g of the crude 6-0-methyl derivative.

(3) In a mixture of 64 ml of dioxane and 10 ml of water was dissolved 12.72 g of the compound obtained in the above item (2), and 636 mg of palladium acetate, 3.0 g of triphenylphosphine and 16 ml of triethylammonium formate were added. After stirring under reflux for 2 hours, the reaction solution was cooled, poured into 200 ml of ether and then washed each once with 200 ml of water and 100 ml of the one, respectively. The aqueous layers were combined, and the pH of the solution was adjusted to about 9 by adding sodium carbonate under ice-cooling. The solution was extracted twice with 300 ml of ether, and then the ether layer was washed with 400 ml of a saturated aqueous sodium chloride solution and dried over anhydrous magnesium sulfate. The solvent was evaporated, the resulting crude product was purified by a silica gel column chromatography (eluent:chloroform:methanol=9:1) and crystallized from ethanolpetroleum ether to give 4.983 g of 6-0-methylerythromycin A 9-oxime.

m.p. 248°–251° C. (melted at 169°–171° C., resolidified at 180°–185° C., and melted again at 248°–251° C.).

$IR\nu_{max}^{KBr}cm^{-1}$: 3400, 1730, 1625.

$^1H$-NMR(400 MH$_Z$, CDCl$_3$)δ=2.29(6H, s, N(CH$_3$)$_2$), 3.11(3H, s, 6-OCH$_3$), 3.33(3H, s, 3''-OCH$_3$).

$^{13}C$-NMR(50.3 MH$_Z$, CDCl$_3$)δ=170.1(C-9), 78.8(C-6), 51.2(C$_6$-OCH$_3$), 49.5(C$_3$''-OCH$_3$), 40.4(N(CH$_3$)$_2$), 25.4(C-8), 20.0(C$_6$-CH$_3$).

Mass (SIMS) m/e=763(MH+).

Elementary analysis for $C_{38}H_{70}N_2O_{13}$: Calcd.(%): C: 59.82, H: 9.25, N: 3.67. Found(%) : C: 59.79, H: 9.10, N: 3.70.

EXAMPLE 2

(1) To a solution of 5 g of erythromycin A 9-oxime in 10 ml of tetrahydrofuran was added 1.2 ml of benzyl bromide, and the mixture was refluxed for 5.5 hours. To the ice-cooled reaction solution was added 10 ml of dimethyl sulfoxide, and then 2 ml of benzyl bromide and 1.01 g of 85% potassium hydroxide powder were added, respectively, under ice-cooling. After stirring at room temperature for 4 hours, the reaction solution was poured into 100 ml of water and extracted twice with 100 ml of ethyl acetate. The solvent was evaporated, and there was obtained the crude product, which was then crystallized from a mixture of ethanol and n-hexane to give 5.02 g of 2'-0,3'-N-dibenzylerythromycin A 9-(0-benzyl)oxime bromide.

(2) In 13.2 ml of dimethyl sulfoxide/tetrahydrofuran (1/1:V/V) was dissolved 3.3 g of the compound obtained in the above item (1), and then 0.57 ml of methyl iodide and 0.26 g of 85% potassium hydroxide powder were added, respectively, under ice-cooling. After stirring for 2 hours, the reaction solution was poured into 100 ml of water and extracted twice with 100 ml of ethyl acetate. The solvent was evaporated, and there was obtained the crude product, which was then crystallized from a mixture of ethyl acetate and cyclohexane to give 2.936 g of the 6-0-methyl derivative.

(3) To a solution of 2.93 g of the compound obtained in the above item (2) in 25 ml of methanol were added 2.3 g of 10% palladium carbon (52.6% wet), 0.305 g of ammonium formate and 1.84 ml of 99% formic acid, and the mixture was stirred at 50° C. for 3 hours. The catalyst was filtered and washed with methanol. The filtrate and washing were combined, and concentrated under reduced pressure. To the residue thus obtained was added 70 ml of an aqueous sodium carbonate solution, and the mixture was extracted twice with 70 ml of ethyl acetate. The organic layer was washed with 140 ml of a saturated aqueous sodium chloride solution and then dried over anhydrous magnesium sulfate. The solvent was evaporated under reduced pressure, and there was obtained 1.75 g of the crude product, which was then crystallized from a mixture of ethanol and petroleum ether to give 1.17 g of 6-0-methylerythromycin A 9-oxime.

The physical data for the melting point, IR, $^1$H-NMR, $^{13}$C-NMR and Mass of this compound were identical with those of the compound obtained in Example 1-(3).

EXAMPLE 3

(1) In 50 ml of a mixture of dimethyl sulfoxide/tetrahydrofuran (1/1:V/V) was dissolved 5 g of erythromycin A 9-oxime, 3.18 ml of benzyl bromide was added, and the mixture was stirred at room temperature for 1.5 hours. To the reaction solution was added 0.737 g of 50% sodium hydride, and the mixture was stirred at room temperature for 2 hours. The reaction solution, after addition of 150 ml of water, was extracted twice with 150 ml of ethyl acetate. The solvent was evaporated to give the crude product, which was then crystallized from a mixture of chloroform and n-hexane, and there was obtained 6.34 g of 2'-0,3'-N-dibenzylerythromycin A 9-(0-benzyl)oxime bromide.

(2) In 20 ml of a mixture of dimethyl sulfoxide/tetrahydrofuran (1/1:V/V) was dissolved 5 g of the compound obtained in the above item (1), and then 0.85 ml of methyl iodide and 0.39 g of 85% potassium hydroxide were added, respectively, under ice-cooling. After stirring for 2 hours, the reaction solution was poured into 100 ml of water and extracted twice with 100 ml of ethyl acetate. The solvent was evaporated, and the residue was washed with 30 ml of petroleum ether and dried to give 5.47 g of the 6-0-methyl derivative.

(3) In 50 ml of N,N-dimethylformamide was dissolved 5 g of the compound obtained in the above item (2), and then 1 g of 10% palladium carbon (52.6% wet) and 5.63 g of ammonium formate were added. After stirring at 50° C. for 3 hours, the reaction mixture was cooled, and the catalyst was separated by filtration and washed with a little amount of methanol. The filtrate and washing were combined, poured into 130 ml of water and extracted twice with 130 ml of ethyl acetate. The organic layer was washed once with 250 ml of a saturated aqueous sodium chloride solution and concentrated. The residue was dissolved in 50 ml of methanol, followed by addition of 4 g of 10% palladium carbon (52.6% wet), 0.52 g of ammonium formate and 3.15 ml of formic acid, and then the mixture was stirred at 50° C. for 3 hours. After cooling the mixture, the catalyst was separated by filtration and washed with methanol. The filtrate and washing were combined and concentrated under reduced pressure. The resulting residue, after addition of 100 ml of an aqueous sodium carbonate solution, was extracted twice with 100 ml of ethyl acetate. The organic layer was washed with 200 ml of a saturated aqueous sodium chloride solution and dried over anhydrous magnesium sulfate. The solvent was evaporated under reduced pressure, and there was obtained 3.26 g of the crude product, which was then crystallized from ethanolpetroleum ether to give 2.07 g of 6-0-methylerythromycin A 9-oxime.

The physical data for the melting point, IR, $^1$H-NMR, $^{13}$C-NMR and Mass of this compound were identical with those of the compound obtained in Example 1-(3).

REFERENTIAL EXAMPLE 3 g of 6-0-methylerythromycin A 9-oxime and 3.27 g of sodium hydrogen sulfite were dissolved in a mixture of 30 ml of ethanol and 30 ml of water, and the solution was refluxed with stirring for 6 hours. The solution was cooled to room temperature, 60 ml of water was added, and the pH of the solution was adjusted to more than 10 with a saturated aqueous sodium carbonate solution. The precipitate which formed was collected by filtration, washed throughly with water and recrystallized from ethanol to give 2.01 g of 6-0-methylerythromycin A. m.p. 223°–225° C.

What is claimed is:

1. A method for the selective methylation of the hydroxy group at the 6-position of erythromycin A derivatives which comprises reacting erythromycin A 9-oxime with a compound represented by the formula R-X (wherein R is a 2-alkenyl group, a benzyl group or a substituted benzyl group, and X is a halogen atom) to give a quaternary salt compound represented by the formula

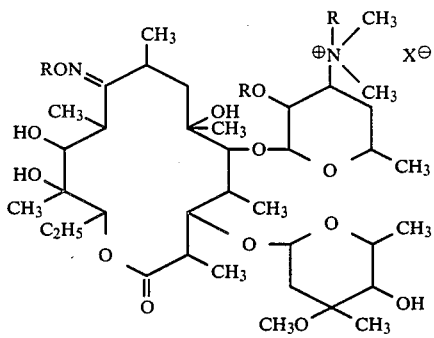

(wherein R and X are as defined above), reacting the resulting compound with a methylating agent to give a 6-0-methylerythromycin A derivative, and eliminating R groups of the resulting compound by hydrogenolysis to give 6-0-methylerythromycin A 9-oxime represented by the formula

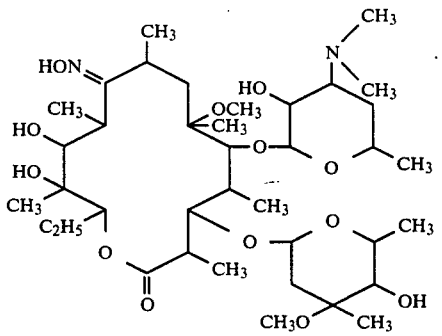

2. A method according to claim 1, wherein the compound of R-X is an allyl halide.

3. A method according to claim 1, wherein the compound of R-X is a benzyl halide.

* * * * *